United States Patent
Shinomiya et al.

[11] Patent Number: 5,880,314
[45] Date of Patent: Mar. 9, 1999

[54] HYDROCHALCONE DERIVATIVES, COSMETIC COMPOSITIONS CONTAINING SAID DERIVATIVES AND METHODS OF PRODUCING THE SAME

[75] Inventors: Tatsuro Shinomiya; Hiroko Kaminaga; Shohei Nozaki, all of Kanagawa; Masahiro Sakamoto, Hokkaido; Shigeharu Morimoto, Kumamoto, all of Japan

[73] Assignee: Mitsui Chemicals, Inc., Tokyo, Japan

[21] Appl. No.: 875,265

[22] PCT Filed: Nov. 25, 1996

[86] PCT No.: PCT/JP96/03444

§ 371 Date: Jul. 18, 1997

§ 102(e) Date: Jul. 18, 1997

[87] PCT Pub. No.: WO97/19044

PCT Pub. Date: May 29, 1997

[30] Foreign Application Priority Data

Nov. 24, 1995 [JP] Japan ................... 7-329668

[51] Int. Cl.⁶ ................ C07C 39/12; C07C 53/00; C07C 69/00
[52] U.S. Cl. .............. 568/729; 554/228; 560/138
[58] Field of Search .............. 568/729; 554/228; 560/138

[56] References Cited

U.S. PATENT DOCUMENTS 4,683,241 7/1987 Miyano et al. ............ 514/512
4,954,659 9/1990 Parkhurst et al. .......... 568/651

FOREIGN PATENT DOCUMENTS 1-139946 6/1993 Japan .

OTHER PUBLICATIONS

Journal of Chemical Society, Perkin Trans. I, (7), (1979), pp. 1661–1664, Matt Karhu et al, "Acid–catalysed Rearrangement of 2,3,4,5–tetrahydrobenz(b)oxepin–2–spirocyclohexa–2',5–dien–4'–one and 3',5',7',9–tetra–t–butyl–2,3,4,5–tetrahydrobenz(b)oxepin–2–spirocyclohexa–2',5'–dien–4'–one. Evidence for Quinone Methide Intermediate".

Journal of Chemical Society, Perkin Trans. I, (1), (1981), pp. 303–306, Matti Karhu et al., "Formation of Diphenyl Ethers from Cyclohexa–2,5–dienones via 4–Phenoxy–4–(1–alkoxy)cyclohexa–2,5–dienones as Probable Intermediates".

Patent Abstracts of Japan, vol. 017, No. 659 (C–1137), Dec. 7, 1993 & JP 05213729 A (Kao Corp), Aug. 24, 1993 *Abstract*.

Database WPI, Section Ch, Week 9436, Derwent Publications Ltd., London, GB; Class B04, AN 94290835 XP002057894 & JP 06219934A (Dowa Mining Co., Ltd.), Aug. 9, 1994 *Abstract*.

Database WPI, Section Ch, Week 9724, Derwent Publications Ltd., London, GB; Class B04, AN 97259816 XP002057895 & CN 1101285A (Feng Weiyuan), Apr. 12, 1995 *Abstract*.

Primary Examiner—Paul J. Killos
Assistant Examiner—Brian J. Davis
Attorney, Agent, or Firm—Burns, Doane, Swecker & Mathis, L.L.P.

[57] ABSTRACT

The present invention can provide cosmetic formulations comprising hydrochalcone compounds of the general formula (I):

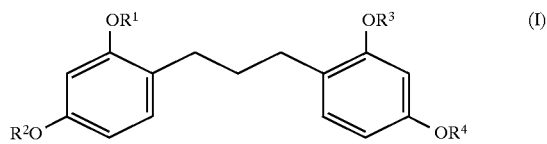

in which $R^1$ to $R^4$ are each independently H or —COR, and R is an alkyl group having 1–20 carbon atoms as effective components, which are highly effective in suppressing pigment deposition and depigmenting the skin and which are very safe to the skin and highly stable during storage.

15 Claims, No Drawings

HYDROCHALCONE DERIVATIVES, COSMETIC COMPOSITIONS CONTAINING SAID DERIVATIVES AND METHODS OF PRODUCING THE SAME

TECHNICAL FIELD

The present invention is related to novel hydrochalcone compounds, cosmetic compositions containing said hydrochalcone compounds as effective components which are very safe to the skin and have good shelf life, and methods of producing the same.

BACKGROUND ART

Ultraviolet rays cause inflammation of the skin mainly in the form of erythema, in which various chemical mediators are released to stimulate melanocytes which promote the synthesis of melanin causing the skin to darken. This darkening is caused by an excessive production of melanin in the melanocytes, then transferred to epidermic cells.

Conventionally, depigmenting cosmetics containing salts and various derivatives of vitamin C, hydroquinone monobenzyl ether, hydrogen peroxide or the like have been proposed to prevent pigment deposition, spots, freckles or the like on the skin and to maintain natural white skin. Further, various plant extracts or plant-derived materials such as gallic acid and geranial or the like have been proposed for use in such cosmetics. Furthermore, hydroquinone or hydrochalcone derivatives such as phlorine, phlorizin, phlorezin (Japanese Patent Laid-open 92/235112), dihydrophloretin (WO95/11662) have been reported to have an effect in suppressing the synthesis of melanin.

However, most of these compounds were found not to be very effective in preventing pigment deposition or in depigmenting the skin because of their poor shelf life when formulated, or their poor efficacy in suppressing inflammation caused by ultraviolet irradiation. Further, when hydroquinone monobenzyl ether or the like are combined in such cosmetics, although skin darkened with deposited pigment can be effectively lightened, there are side effects such as skin allergies and irritation or other problems. Furthermore, the various plant extracts have problems, such that their efficacy is not quite satisfactory, or the quality of the extracts is not always consistent.

Furthermore, although it has been reported in U.S. Pat. No. 4,954,659 that hydrochalcone compounds have antioxidative activity, their potential usefulness in cosmetics has not been disclosed.

Thus, it is very difficult to obtain cosmetics which are highly effective in suppressing pigment deposition and depigmentation and which are very safe to the skin and have good shelf life. Therefore, development of cosmetics satisfying these was desirous.

DISCLOSURE OF INVENTION

Accordingly, under these circumstances, the present inventors carried out intensive research to resolve the problems in the conventional technology. As a result, the inventors have found that extracts obtained from plants of *Dioscorea composita* are highly active in inhibiting tyrosinase activity, are very safe to the skin, and are sufficiently stable during storage when combined in various cosmetic formulations.

Furthermore, the present inventors have found that an active component in said extracts is a novel hydrochalcone compound, and that synthetic compounds and esterified compounds of said hydrochalcone compound are highly active in inhibiting tyrosinase activity, are very safe to the skin, and are sufficiently stable during storage when combined in various cosmetic formulations. Thus the present invention has been completed.

Namely, hydrochalcone compounds of the present invention have the following formula (I):

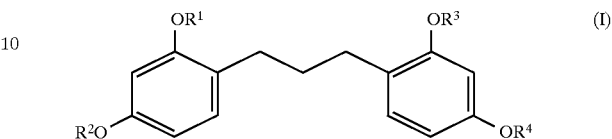

in which
$R^1$ to $R^4$ are each independently H or —COR, and R is an alkyl group having 1–20 carbon atoms.

Cosmetic compositions of the present invention comprise a hydrochalcone compound represented by formula (I) above as an effective component.

Hydrochalcone compounds of formula (I) above can be obtained by extracting *Dioscorea composita* plants with suitable solvents to obtain extracts containing the above-mentioned hydrochalcone derivatives. Furthermore, these extracts or hydrochalcone compounds isolated and purified from these extracts can be used as effective components in cosmetic compositions.

BEST MODE FOR CARRYING OUT THE INVENTION

Embodiments of the present invention are explained more in detail as follows.

Synthesis of hydrochalcone compounds of formula (I) above can be carried out by known methods. For example, the compounds can be appropriately synthesized according to the method described in J. Chem. Soc., Perkin Trans. 1 (1979), (7), 1661–4 or J. Chem. Soc., Perkin Trans. 1 (1981), (1), 303–6. That is, the compounds can be produced by the aldol condensation of a hydroxybenzaldehyde derivative or its hydroxyl-blocked compound and a hydroxyacetophenone derivative or its hydroxyl-blocked compound to obtain a chalcone derivative, followed by deblocking, hydrogenation and carbonyl reduction.

The method to block the hydroxyl groups of hydroxybenzaldehyde derivatives and hydroxyacetophenone derivatives to be used in the abovementioned synthesis is not particularly limited. In general, the benzyl ether method is used, in which, for example, a benzyloxybenzaldehyde derivative or benzyloxyacetophenone derivative having blocked hydroxyl groups can be easily obtained by reaction with a benzyl halide under alkaline conditions according to the conventional method.

The base to be used in the aldol condensation in this synthesis is not particularly limited. For example, an alkaline metal hydroxide or an alkaline metal alcoholate can be used.

Examples of hydrochalcone compounds of the present invention include 1,3-bis(2,4-dihydroxyphenyl)propane, 1-(2,4-dihydroxyphenyl)-3-(4-hydroxy-2-acetoxyphenyl) propane, 1-(2,4-dihydroxyphenyl)-3-(2-hydroxy-4-acetoxyphenyl)propane, 1-(2,4-dihydroxyphenyl)-3-(2,4-diacetoxyphenyl)propane, 1,3-bis(4-hydroxy-2-acetoxyphenyl)propane, 1-(2-hydroxy-4-acetoxyphenyl)-3-(4-hydroxy-2-acetoxyphenyl)propane, 1-(4-hydroxy-2-acetoxyphenyl)-3-(2,4-diacetoxyphenyl)propane, 1-(2-hydroxy-4-acetoxyphenyl)-3-(2,4-diacetoxyphenyl)

propane, 1,3-bis(2-hydroxy-4-acetoxyphenyl)propane, 1,3-bis(2,4-diacetoxyphenyl)propane, 1,3-bis(2-hydroxy-4-ethanoyloxyphenyl)propane, 1,3-bis(2,4-diethanoyloxyphenyl)propane, 1,3-bis(2-hydroxy-4-butanoyloxyphenyl)propane, 1,3-bis(2,4-dibutanoyloxyphenyl)propane, 1,3-bis(2-hydroxy-4-octanoyloxyphenyl)propane, 1,3-bis(2,4-dioctanoyloxyphenyl)propane, 1,3-bis(2-hydroxy-4-dodecanoyloxyphenyl)propane, 1,3-bis(2,4-didodecanoyloxyphenyl)propane, 1,3-bis(2-hydroxy-4-hexadecanoyloxyphenyl)propane, 1,3-bis(2,4-dihexadecanoyloxyphenyl)propane, 1,3-bis(2-hydroxy-4-octadecanoyloxyphenyl)propane and 1,3-bis(2,4-dioctadecanoyloxyphenyl)propane.

In cosmetic compositions of the present invention, hydrochalcone compounds of formula (I) above can be contained alone or in combination of two or more. The amount to be contained is not particularly limited; however, 0.0001% to 20% by weight, in particular 0.001% to 10% by weight of the total composition is preferable. With this range, the cosmetic compositions can achieve the efficacy of the present invention, provide a smooth feel on the skin upon use, and provide good shelf life in a variety of formulations.

In preparing cosmetic compositions which contain hydrochalcone compounds of formula (I) above as effective components, chemically synthesized compounds can be used as said derivatives; however, 1,3-bis(2,4-dihydroxyphenyl)propane and its derivative extracted from plants of *Dioscorea composita* of the genus Dioscorea of the family Dioscoreaceae, which are naturally grown or cultured mainly in Central America and India can be used.

Solvents to be used to obtain extracts of these plants generally include water, alcohols such as methanol, ethanol and isopropyl alcohol, polyhydric alcohols such as ethylene glycol, propylene glycol and 1,3-butylene glycol, ketones such as acetone, esters such as ethyl acetate, ethers such as diethyl ether and aromatic compounds such as benzene. These solvents can be used alone or in combination of two or more.

Generally fresh or dried plants of *Dioscorea composita* are used whole or chopped. For extraction, 100 parts of the abovementioned solvents per 5 to 50 parts by dry weight of the plants are preferably used.

Extraction can be carried out at room temperature or with applied heat using an ordinary extractor, a Soxhlet extractor or the like. Extraction time is not particularly limited; however, a period of 1 hour to 1 week is generally preferable.

In order to obtain 1,3-bis(2,4-dihydroxyphenyl)propane from the extracts of plants of *Dioscorea composita*, customary isolation and purification methods, for example, fractionation using a solvent (or a mixture of solvents) which is different from the one used for extraction and of low compatibility, column chromatography or the like using an ion-exchange resin can be used.

Examples of the form, in which 1,3-bis(2,4-dihydroxyphenyl)propane obtained from the extract of *Dioscorea composita* plants can be used as an effective component in cosmetic compositions, include the unprocessed extract or its purified form, or processed products which are obtained by various processes, for example, a concentrated liquid obtained by concentrating the extract under normal or reduced pressure, or a solid obtained by evaporating the solvent in said concentrated liquid to dryness. Also, solids obtained by filtration and drying after precipitation from the concentrated liquid, or solids prepared by lyophilization of the concentrated liquid may be used. Furthermore, 1,3-bis(2,4-dihydroxyphenyl)propane obtained from the extract can be used after esterification. For esterification, an esterifying agent which can introduce the —COR group in formula (I) can be used.

The amount (calculated as dry weight) of extract from a *Dioscorea composita* plant to be contained in a cosmetic composition is not particularly limited; however 0.01 to 5.0% by weight of the total composition is preferable. With this range, the cosmetic compositions can achieve the efficacy of the present invention, provide a smooth feel on the skin upon use, and yield good shelf life in a variety of formulations.

Cosmetic compositions of the present invention can be prepared in combination with various cosmetic bases according to conventional methods in such forms as cosmetic lotions including softening lotions, astringent lotions and cleansing lotions, emulsions such as emollient emulsions, moisturizing emulsions, nourishing emulsions and cleansing emulsions, creams such as emollient creams, moisturizing creams, massage creams, cleansing creams and makeup creams, makeup cosmetics such as lip creams and foundations, packs, and facial cleansing agents.

Furthermore, cosmetic compositions of the present invention can be appropriately combined with auxiliaries in a certain range of concentrations so as to achieve the objective of the present invention. Examples of such auxiliaries include pigments such as tar-based pigments and iron oxide, preservatives such as paraben, anionic surface-active agents such as fatty acid soaps, sodium cetyl sulfate and sodium N-stearoyl-L-glutamate, nonionic surface-active agents such as polyoxyethylenealkyl ether, polyoxyethylene fatty acid esters, polyoxyethylene polyhydric alcohol fatty acid esters, polyoxyethylene hydrogenated castor oil, polyhydric alcohol fatty acid esters and polyglycerin fatty acid esters, cationic surfactants such as tetraalkyl ammonium salts, betaine type, sulfobetaine type and sulfoamino acid type ampholytic surface-active agents, natural surface-active agents such as lecithin and lysophosphatidylcholine, pigments such as titan oxide, anti-oxidants such as dibutylhydroxytoluene, chelating agents, various vitamins, water, alcohols, ultraviolet absorbents, perfumes, preservatives, oils, wetting agents, moisturizing agents, thickening agents, various amino acids, and various animal or plant extracts. Furthermore, depigmenting components such as ascorbic acid, ascorbic acid derivatives, kojic acid and arbutin can be added.

Cosmetic compositions containing the abovementioned components can be provided as pharmaceutical cosmetics or non-medicinal products, such as suntan lotions or creams and sunscreen formulations.

The present invention will be explained in more detail in the Examples and Comparative Examples below. However, the present invention is not limited by these examples. Test methods used in the present invention, i.e., (a) tyrosinase activity inhibition test, (b) skin color lightness recovery test, (c) bleaching practical test, (d) light patch test and (e) stability test are as follows:

(a) Tyrosinase Activity Inhibition Test 1 ml of a tyrosine solution (0.3 mg/ml) and 0.9 ml of each sample solution (Examples, Comparative Examples) were added to 1 ml of a McIlvaine's buffer solution (pH 6.8), the admixture was preheated at a temperature of 37° C. for 10 minutes. 0.1 ml of tyrosinase (Sigma, 1 mg/ml) was then added and the resultant admixture was kept at 37° C. for 15 minutes, after which absorbance (A) was measured at 475 nm using a photometer. Similarly, absorbance (B) of an admixture in which 0.1 ml of the buffer solution was added in place of tyrosinase, absorbance (C) of an admixture in which 0.9 ml of the buffer solution was added in place of a sample solution, and absorbance (D) of an admixture in which 1.0 ml of the buffer solution was added in place of a sample solution and tyrosinase were measured. An inhibition rate (%) was calculated as follows:

Inhibition rate (%)=[1-(A-B)/(C-D)]×100

(b) Skin Color Lightness Recovery Test

The skin in the medial surface of the right and left brachia of 20 test human subjects was irradiated consecutively for 3 days with ultraviolet rays in the UVB region, at 1.2 times the minimum dose which causes erythema. One week after the first irradiation, standard skin lightness values ($L_0$, $L_0'$) for the sample application regions of the Examples and for the base application regions in the Comparative Examples were measured. Subsequently, samples and bases were applied 3 times a day. After 2 and 4 weeks from the start of application, skin lightness values ($L_n$, $L_n'$) of the skin applied with samples and bases were measured to evaluate the degree of recovery of the skin to its pre-erythema state according to the evaluation criteria (Table 1). The lightness of the skin was measured using a chromatic meter (Type CR-321, Minolta). The evaluation was expressed by an average score of 20 subjects after 4 weeks of application.

TABLE 1

| Judging criteria Sample having the difference of the skin color lightness which meets the following formula | Evaluation score |
| --- | --- |
| $\Delta L - \Delta L' \geq 4.0$ |  |
| $\Delta L$: Recovery value at sample application site ($L_n - L_0$) $\Delta L'$: Recovery value at base application site ($L_n' - L_0'$) | 5 |
| $4.0 > \Delta L - \Delta L' \geq 2.5$ | 4 |
| $2.5 > \Delta L - \Delta L' \geq 1.5$ | 3 |
| $1.5 > \Delta L - \Delta L' \geq 0.5$ | 2 |
| $0.5 > \Delta L - \Delta L'$ | 1 |

(c) Practical Skin Decoloring Test

The skin of the inner joint of the arm and the forearm of test human subjects (20) was exposed to the summer sun for 3 hours (1.5 hours a day for 2 days). Samples of Examples and bases of the Comparative Examples were applied to the test sites on the right and left arms, respectively, in the morning and in the evening after the day of the exposure for consecutive 8 weeks. Evaluation was made by the number of the subjects in which the skin decoloring effect was higher at the sample application site than at the base application site.

(d) Light Patch Test

Straps for a patch test (1.1 cm in diameter) on which 0.05 g each of samples of the Examples and the Comparative Examples was applied were placed on the skin of the inner joint of the arm and the forearm of 25 human subjects for 24 hours. After removing the straps, the test sites were exposed to summer sunlight for 6 hours (3 hours a day for 2 days). Evaluation was made by examining the skin of 25 subjects according to the criteria in Table 2. Results were expressed by the number of subjects which were judged as (±) or more 24 hours after the final exposure.

TABLE 2

| Criteria | Evaluation |
| --- | --- |
| erythema, edema, blister. | (+++) |
| erythema, edema. | (++) |
| erythema. | (+) |
| light erythema | (±) |
| no reaction | (−) |

(e) Stability Test

Samples of the Examples and the Comparative Examples were placed in a thermostat at a temperature of 45° C. and a day-depending observation was carried out. The evaluation was made according to the criteria shown in Table 3. In the Table, "abnormality" means conditions in which change in color or odor is found, or precipitation in a lotion or phase separation in an emulsion is observed.

TABLE 3

| Criteria | Evaluation |
| --- | --- |
| Abnormality was observed in 10 days | X |
| Abnormality was observed in 1 month | Δ |
| Abnormality was observed in 3 months | ○ |
| Abnormality was not observed in 4 months | ⊙ |

PRODUCTION EXAMPLE 1

(Production of *Dioscorea composita* Extract I)

100 g of a dried *Dioscorea composita* plant were placed in 1 L of a water/ethanol (1:1 by volume) solvent. Extraction was carried out at room temperature for 24 hours with stirring, after which the extract was filtered, and the resultant filtrate was lyophilized to obtain 28 g of a powdery solid.

PRODUCTION EXAMPLE 2

(Production of *Dioscorea composita* Extract II)

100 g of a dried *Dioscorea composita* plant were placed in 1 L of 100% ethyl acetate. Extraction was carried out at room temperature for 4 hours with stirring, after which the extract was filtered, and the resultant filtrate was concentrated at 50° C. to dry to solid to obtain 6 g of a powdery solid.

EXAMPLES 1 TO 4 AND COMPARATIVE EXAMPLE 1

(Two-Phase Type Lotion)

Two-phase type lotions having ingredients shown in Table 4 and an effective compound as shown in Table 5 were prepared and the abovementioned tests were carried out with them.

TABLE 4

| Ingredients | Content (% by weight) |
| --- | --- |
| (A) Olive oil | 15.0 |
| Isopropyl myristate | 5.0 |
| Polyoxyethylenenonyl-phenol ether (2 E.O.) | 0.5 |
| (B) *Dioscorea composita* Extract I | As shown in Table 5 |
| (C) *Dioscorea composita* Extract II | As shown in Table 5 |
| (D) Glycerine | 5.0 |
| Methylparaben | 0.1 |

TABLE 4-continued

| Ingredients | Content (% by weight) |
| --- | --- |
| Ethanol | 7.0 |
| Purified water | To make 100% |

(1) Preparation Method

Using quantities as shown in Table 4, components (A) were homogeneously mixed, then component (B) was homogeneously dissolved into the resultant mixture. Next, components (D) were homogeneously mixed then dispersed with stirring into the first mixture, and the resultant admixture was filled into a container to produce a formulation containing Extract I.

Similarly, Using quantities as shown in Table 4, components (A) were homogeneously mixed, then component (C) was homogeneously dissolved into the resultant mixture. Next, components (D) were homogeneously mixed then dispersed with stirring into the first mixture and the resultant admixture was filled into a container to produce a formulation containing Extract II.

The formulations were homogeneously dispersed with shaking immediately before use.

(2) Characteristics

Results of the tests (a) to (e) are shown in Table 5.

TABLE 5

| Type of Extract and its content (wt %) | Tyrosinase activity inhibition test (Inhibition rate, %) | Skin lightness recovery test | Skin decoloring test (Number of subjects) | Light patch test (Number of subjects) | Stability |
| --- | --- | --- | --- | --- | --- |
| Example 1 Extract I 0.05% | 93.0 | 3.45 | 12 | 0 | ⊚ |
| Example 2 Extract I 1.00% | 100.0 | 4.00 | 16 | 0 | ⊚ |
| Example 3 Extract II 0.05% | 95.3 | 3.40 | 12 | 0 | ⊚ |
| Example 4 Extract II | 100.0 | 4.10 | 16 | 0 | ⊚ |
| Comparative Example 1 None | 0 | 1.15 | 1 | 0 | ⊚ |

As shown in Table 5, Comparative Example 1 did not give any good results in any tests.

In contrast, cosmetic compositions of the present invention in Examples 1 to 4 showed good results in all the tests, and did not cause irritation on the skin in any tests on the human skin.

Examples 5 to 8 and Comparative Example 2
(Skin Cream)

Skin creams having ingredients shown in Table 6 and an effective compound as shown in Table 7 were prepared and the abovementioned tests were carried out with them.

TABLE 6

| Ingredients | Content (% by weight) |
| --- | --- |
| (A) Squalane | 10.0 |
| Olive oil | 10.0 |
| Solid paraffin | 5.0 |
| Cetanol | 4.0 |
| Sorbitan monostearate | 2.0 |
| Polyoxyethylene sorbitan monostearate (20 E.O.) | 2.0 |
| (B) *Dioscorea composita* Extract I | As shown in Table 7 |
| (C) *Dioscorea composita* Extract II | As shown in Table 7 |
| (D) Glycerine | 5.0 |
| Methylparaben | 0.1 |
| Purified water | To make 100% |

(1) Preparation Method

Using quantities as shown in Table 6, components (A) were mixed, then component (B) was homogeneously dissolved into the resultant mixture with heat to make the temperature 80° C. Next, components (D) were injected then mixed with stirring into the first mixture, and the resultant admixture was cooled to 30° C. with stirring to produce a product containing Extract I.

Similarly, using quantities as shown in Table 6, components (A) were mixed, then component (C) was homogeneously dissolved into the resultant mixture with heat to make the temperature 80° C. Next, components (D) were injected then mixed with stirring into the first mixture, and the resultant admixture was cooled to 30° C. with stirring to produce a product containing Extract II.

(2) Characteristics

Results of the tests (a) to (e) are shown in Table 7.

TABLE 7

| Type of Extract and its content (wt %) | Tyrosinase activity inhibition test (Inhibition rate, %) | Skin lightness recovery test | Skin decoloring test (Number of subjects) | Light patch test (Number of subjects) | Stability |
|---|---|---|---|---|---|
| Example 5 Extract I 0.50% | 100.0 | 3.70 | 15 | 0 | ◎ |
| Example 6 Extract I 2.00% | 100.0 | 4.15 | 18 | 0 | ◎ |
| Example 7 Extract II | 100.0 | 3.85 | 15 | 0 | ◎ |
| Example 8 Extract II 2.00% | 100.0 | 4.20 | 19 | 0 | ◎ |
| Comparative Example 2 None | 0 | 1.10 | 1 | 0 | ◎ |

As shown in Table 7, Examples 5 to 8 markedly showed good results in all the tests, and did not cause irritation on the skin in any tests on the human skin.

PRODUCTION EXAMPLE 3
(Example of Synthesis of 1,3-bis(2,4-dihydoxyphenyl)propane)

6.36 g (20 mmol) of 2,4-dibenzyloxybenzaldehyde and 6.64 g (20 mmol) of 2,4-dibenzylacetophenone were suspended in 80 ml of methanol, 1.15 g of metal sodium in methanol (10 ml) was added dropwise to the suspension and the resultant suspension was reacted at room temperature for 10 hours. The resultant precipitate was filtered, washed with methanol, then dried to obtain 2,4,2',4'-tetrabenzyloxychalcone. The yield was 11.50 g.

2,4,2',4'-Tetrabenzyloxychalcone thus obtained was dissolved in tetrahydrofuran and ethanol, Raney nickel catalyst was added to the solution, and the admixture was reacted at room temperature while blowing hydrogen gas for 20 hours. After the reaction, the catalyst was filtered off, the resultant filtrate was concentrated to obtain crude 1,3-(2,4-dihydroxyphenyl)propane.

Major component was fractionated by column chromatography using chloroform/acetone (30/1 by volume) and ethyl acetate/ethanol (25/1 by volume). The yield was 1.21 g.

Results of $H^1$-NMR measurements are as follows:

TABLE 8

| δ | Proton ratio | Group |
|---|---|---|
| 1.62 | 2 | φ-CH$_2$CH$_2$ CH$_2$-φ |
| 2.4 | 4 | φ-CH$_2$ CH$_2$ CH$_2$-φ |
| 6.12 | 2 | o-m Coupling (1, 2, 4 substitute) |
| 6.26 | 2 | m-p Coupling (1, 2, 4 substitute) |
| 6.78 | 2 | o-p Coupling (1, 2, 4 substitute) |
| 8.9, 9.0 | 4 | —OH |

PRODUCTION EXAMPLE 4
(Synthesis of 1,3-bis(2,4-diacetoxyphenyl)propane)

24.9 g (0.1 mol) of 1,3-bis(2,4-dihydroxyphenyl)propane were dissolved in 100 ml of ethyl acetate, 49.0 g (0.48 mol) of acetic acid anhydrous and 1.58 g (0.02 mol) of pyridine were added to this solution and the resultant admixture was refluxed for 3 hours. 50 g of water were added to the reaction mixture thus obtained and the admixture was extracted and washed, the resultant ethyl acetate layer was dried with sodium sulfate anhydrous, and ethyl acetate was evaporated by evaporator to obtain 40.87 g of 1,3-bis(2,4-diacetoxyphenyl)propane (yield 98.0%).

Results of $H^1$-NMR measurements of the resultant crystals are as follows:

TABLE 9

| δ | Proton ratio | Group |
|---|---|---|
| 1.83 | 2 | φ-CH$_2$—CH$_2$—CH$_2$-φ |
| 2.21, 2.26 | 12 | —O—CO—CH$_3$ |
| 2.52 | 4 | φ-CH$_2$—CH$_2$—CH$_2$-φ |
| 6.86, 6.95, 7.22 | 6 | Aromatic proton |

PRODUCTION EXAMPLE 5
(Synthesis of 1,3-bis(2,4-didodecanoyloxyphenyl)propane)

24.9 g (0.1 mol) of 1,3-bis(2,4-dihydroxyphenyl)propane, 200 ml of toluene and 47.4 g (0.60 mol) of pyridine were mixed, 105.0 g (0.48 mol) of lauroylic acid chloride were added dropwise to the mixture, and the admixture was reacted under reflux for 1 hour. 1N HCl (500 ml) and chloroform (1 L) were added to the resultant reaction mixture and the chloroform layer was separated by fractionation. The chloroform layer thus obtained was concentrated, chloroform and toluene were removed from the concentrated fraction, and the liquid thus obtained was purified using column chromatography (chloroform/carbon tetrachloride= 3/1 by volume).

Results of $H^1$-NMR measurements of the resultant crystals are as follows:

TABLE 10

| δ | Proton ratio | Group |
|---|---|---|
| 0.90 | 12 | —O—CO—CH$_2$CH$_2$(CH$_2$)$_8$—CH$_3$ |
| 1.25–1.43 | 64 | —O—CO—CH$_2$CH$_2$(CH$_2$)$_8$—CH$_3$ |
| 1.76 | 8 | —O—CO—CH$_2$CH$_2$(CH$_2$)$_8$—CH$_3$ |
| 1.83 | 2 | φ-CH$_2$—CH$_2$—CH$_2$-φ |
| 2.45–2.53 | 12 | —O—CO—CH$_2$CH$_2$(CH$_2$)$_8$—CH$_3$ and |

TABLE 10-continued

| δ | Proton ratio | Group |
|---|---|---|
| 6.83, 6.91, 7.20 | 6 | φ-CH₂—CH₂—CH₂-φ<br>Aromatic proton |

PRODUCTION EXAMPLE 6
(Isolation of 1,3-bis(2,4-dihydroxyphenyl)propane 100 g of a *Dioscorea composita* plant were placed in 1 L of 100% ethyl acetate. Extraction was carried out at room temperature for 4 hours with stirring, after which the extract was filtered. The filtrate was developed using Wako gel C-200 to obtain a fraction of 1,3-bis(2,4-dihydroxyphenyl) propane. After concentration, the fraction was dissolved in ethanol, then added with 1% active carbon. After stirring for 1 hour, the fraction was concentrated using an evaporator to obtain 1,3-bis(2,4-dihydroxyphenyl)propane.

EXAMPLES 9 TO 17
(Melanoma Cell Depigmenting Test)

Effect of compounds in suppressing melanin pigment synthesis was tested by measuring change in color of B16 melanoma cells when the cells were cultured at a concentration which had no adverse effect on growth of the cells. B16 Melanoma cells ($1 \times 10^5$) were inoculated on 60 mm petri dishes. After 24 hours, 1,3-bis(2,4-dihydroxyphenyl) propane synthesized in Production Example 3, 1,3-bis(2,4-diacetoxyphenyl)propane synthesized in Production Example 4 and 1,3-bis(2,4-didodecanoyloxyphenyl)propane were added to the each medium, and incubation was curried out for 5 days. After incubation, the cells recovered by trypsin treatment were suspended in 0.3 ml of phosphate buffer and subjected to ultrasonic treatment for cell disruption, 0.3 ml of 4N NaOH was added to the treated suspension and the resultant suspension was incubated at 60° C. for 2 hours. Absorbance was measured at 400 nm and the amount of released melanin was calculated by setting the control as 100%. Results are shown in Table 11. In Comparative Examples, similar tests were carried out using dihydrophloretin, a hydrochalcone compound, in place of the compounds of the present invention.

As shown in Table 11, compounds of the present invention suppressed release of melanin from B16 melanoma cells at low concentrations as compared to dihydrophloretin in Comparative Examples 3 to 5.

EXAMPLES 18 AND 19 AND COMPARATIVE EXAMPLE 6

(Preparation of Two-Phase Type Lotion)

Two-phase type lotions having ingredients shown in Table 12 and an effective compound as shown in Table 13 were prepared and the abovementioned tests (a) to (e) were carried out with them.

| Ingredients | Content (% by weight) |
|---|---|
| (A) Olive oil | 15.0 |
| Isopropyl myristate | 5.0 |
| Polyoxyethylenenonylphenol ether (2 E.O.) | 0.5 |
| (B) 1,3-bis(2,4-dihydroxyphenyl)propane (Production Example 3) | As shown in Table 13 |
| (C) Glycerine | 5.0 |
| Methylparaben | 0.1 |
| Ethanol | 7.0 |
| Purified water | To make 100% |

(1) Preparation Method

Using quantities as shown in Table 12, component (B) (at 0.01% by weight or 0.2% by weight) was homogeneously mixed with components (A). Next, components (C) were homogeneously blended then dispersed with stirring into the first mixture based on (A), and the resultant admixture was filled into a container to obtain a product.

The content was homogeneously dispersed with shaking immediately before use.

(2) Characteristics

Results of tests are shown in Table 13.

TABLE 11

| | Name of compound added | Amount added (μg/ml) | Melanin production (%) |
|---|---|---|---|
| Example 9 | 1,3-bis(2,4-dihydroxyphenyl)propane | 0.01 | 31 |
| Example 10 | 1,3-bis(2,4-dihydroxyphenyl)propane | 0.03 | 10 |
| Example 11 | 1,3-bis(2,4-dihydroxyphenyl)propane | 0.30 | 7 |
| Example 12 | 1,3-bis(2,4-diacetoxyphenyl)propane | 0.01 | 44 |
| Example 13 | 1,3-bis(2,4-diacetoxyphenyl)propane | 0.03 | 18 |
| Example 14 | 1,3-bis(2,4-diacetoxyphenyl)propane | 0.30 | 11 |
| Example 15 | 1,3-bis(2,4-didodecanoyloxyphenyl)propane | 0.01 | 28 |
| Example 16 | 1,3-bis(2,4-didodecanoyloxyphenyl)propane | 0.03 | 9 |
| Example 17 | 1,3-bis(2,4-didodecanoyloxyphenyl)propane | 0.30 | 7 |
| Comparative Example 3 | Dihydrophloretin | 0.01 | 92 |
| Comparative Example 4 | Dihydrophloretin | 0.03 | 80 |
| Comparative Example 5 | Dihydrophloretin | 0.30 | 65 |

TABLE 13

| Type of Extract and its content (% by weight) | Tyrosinase activity inhibition test (Inhibition rate, %) | Skin lightness recovery test | Skin decoloring test (Number of subjects) | Light patch test (Number of subjects) | Stability |
| --- | --- | --- | --- | --- | --- |
| Example 18 0.01% | 100.0 | 3.85 | 16 | 0 | ◉ |
| Example 19 0.20% | 100.0 | 4.10 | 19 | 0 | ◉ |
| Comparative Example 6 None | 0 | 1.10 | 1 | 0 | ◉ |

As shown in Table 13, Comparative Example 6 did not show any good results in any tests. In contrast, cosmetic compositions of the present invention in Examples 18 and 19 evidently showed good results in all the tests, and did not cause irritation on the skin in any tests on the human skin.

EXAMPLES 20 AND 21, AND COMPARATIVE EXAMPLE 7

(Preparation of Skin Cream)

Skin creams having ingredients shown in Table 14 and an effective compound as shown in Table 15 were prepared and the abovementioned tests were carried out with them.

TABLE 14

| Ingredients | Content (% by weight) |
| --- | --- |
| (A) Squalane | 10.0 |
| Olive oil | 10.0 |
| Solid paraffin | 5.0 |
| Cetanol | 4.0 |
| Sorbitan monostearate | 2.0 |
| Polyoxyethylene sorbitan monostearate (20E.O.) | |
| (B) 1,3-bis(2,4-dihydroxyphenyl)propane (Production Example 6) | As shown in Table 15 |
| (C) Glycerine | 5.0 |
| Methylparaben | 0.1 |
| Purified water | To make 100% |

(1) Preparation Method

Using quantities shown in Table 14, component (B) (0.01% or 0.2% by weight) was homogeneously dissolved then mixed with components (A) with heat to make the temperature of the mixture 80° C. Next, component (C) was injected then mixed with stirring into the first mixture based on (A), and the resultant admixture was cooled to 30° C. while stirring to produce a formulation.

(2) Characteristics

Results of tests are shown in Table 15.

TABLE 15

| Type of Extract and its content (% by weight) | Tyrosinase activity inhibition test (Inhibition rate, %) | Skin lightness recovery test | Skin decoloring test (Number of subjects) | Light patch test (Number of subjects) | Stability |
| --- | --- | --- | --- | --- | --- |
| Example 20 0.01% | 100.0 | 4.15 | 18 | 0 | ◉ |
| Example 21 0.20% | 100.0 | 4.20 | 19 | 0 | ◉ |
| Comparative Example 7 None | 0 | 1.30 | 1 | 0 | ◉ |

As shown in Table 15, Examples 20 and 21 evidently showed good results in all the tests, and did not cause irritation on the skin in any tests on the human skin.

POTENTIAL APPLICABILITY IN INDUSTRY

As mentioned above, the compounds and cosmetic compositions of the present invention are highly effective in suppressing pigment deposition on the skin caused by ultraviolet irradiation, have an efficacy in readily discoloring pigment precipitated on the skin, cause no skin irritation and are sufficiently stable during storage. Namely, the present invention can provide cosmetic compositions having such excellent characteristics.

What is claimed is:

1. Hydrochalcone compounds of the formula (I):

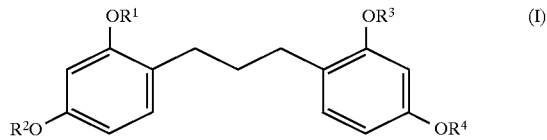

in which
$R^1$ to $R^4$ are each independently H or —COR, and R is an alkyl group having 1–20 carbon atoms.

2. 1,3-bis(2,4-dihydroxyphenyl) propane of the formula (II):

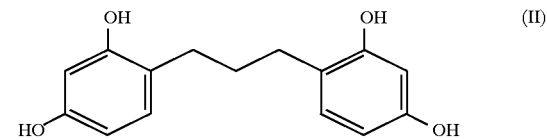

3. A cosmetic composition comprising an effective amount of a hydrochalcone compound of the formula (I) as claimed in claim 1 and a cosmetic base.

4. A cosmetic composition comprising an effective amount of 1,3-bis(2,4-dihydroxyphenyl)propane as claimed in claim 2 and a cosmetic base.

5. A method of producing hydrochalcone compounds of the formula (I):

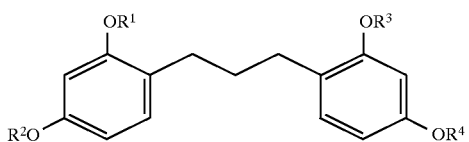

in which
$R^1$ to $R^4$ are each independently H or —COR, and R is an alkyl group having 1–20 carbon atoms,
which comprises a step of chemically synthesizing said hydrochalcone compounds.

6. A cosmetic composition comprising a hydrochalcone compound obtained by the method as claimed in claim 5 and a cosmetic base.

7. A method of producing a cosmetic composition comprising a hydrochalcone compound of the formula (I):

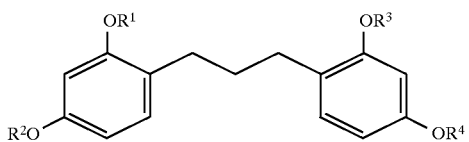

in which
$R^1$ to $R^4$ are each independently H or —COR, and R is an alkyl group having 1–20 carbon atoms, as an effective component, which comprises
  (a) extracting *Dioscorea composita* plants with suitable solvents to obtain an extract comprising said hydrochalcone compound, and
  (b) mixing said extract with a cosmetic base to obtain the cosmetic composition.

8. A method of producing a cosmetic composition comprising a hydrochalcone compound of the formula (I):

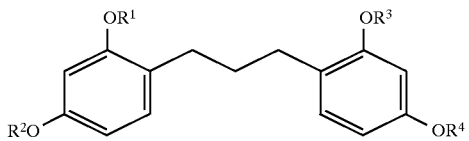

in which
$R^1$ to $R^4$ are each independently H or —COR, and R is an alkyl group having 1–20 carbon atoms, as an effective component, which comprises
  a) a step of extracting *Dioscorea composita* plants with suitable solvents to obtain an extract containing said hydrochalcone compound,
  b) a step of isolating and purifying said hydrochalcone compound from said extract, and
  c) a step of mixing said purified hydrochalcone compound with a cosmetic base to obtain the cosmetic composition.

9. A method of treating pigment deposition and depigmentation of the skin, in which an effective amount of a hydrochalcone compound as claimed in claim 1 is applied on the human skin.

10. Chemically synthesized 1,3-bis(2,4-dihydroxyphenyl)propane of the formula (II):

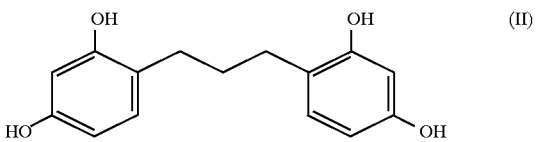

11. A cosmetic composition comprising a hydrochalcone compound obtained by the method as claimed in claim 10 and a cosmetic base.

12. Isolated and purified hydrochalcone compounds of the formula (I):

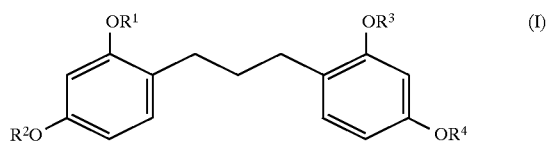

in which
$R^1$ to $R^4$ are each independently H or —COR, and R is an alkyl group having 1–20 carbon atoms.

13. A method of treating pigment deposition and depigmentation of skin, comprising applying to the skin a hydrochalcone compound as claimed in claim 12 in an amount effective for treating pigment deposition and depigmentation.

14. A method of treating pigment deposition and depigmentation of skin, comprising applying to the skin a chemically synthesized hydrochalcone compound as claimed in claim 1 in an amount effective for treating pigment deposition and depigmentation.

15. A method of producing a cosmetic composition comprising a hydrochalcone compound of the formula (I):

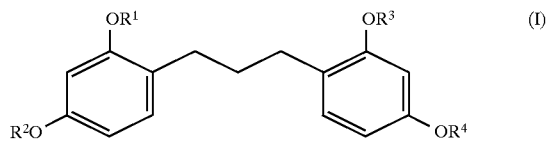

in which
$R^1$ to $R^4$ are each independently H or —COR, and R is an alkyl group having 1–20 carbon atoms, as an effective component, which method comprises
  (a) chemically synthesizing said hydrochalcone compound, and
  (b) mixing said hydrochalcone compound with a base to obtain a cosmetic composition.

* * * * *